US007138227B2

(12) United States Patent
Kusakabe et al.

(10) Patent No.: US 7,138,227 B2
(45) Date of Patent: Nov. 21, 2006

(54) FROZEN SPERMATOZOA COMPOSITIONS AND USES THEREOF

(76) Inventors: Hirokazu Kusakabe, Elm Hokuohkan, Room No. 102, 3-4-1-3 Kyokushin, Asahikawa, Hokkaido 078-8373 (JP); Monika Anna Sczcygiel, 3029 Lowrey Ave., #F1224, Honolulu, HI (US) 96822; David Gordon Whittingham, 5 Wildcroft Manor, Wildcroft Road, Putney Heath, London SW15 3TS (GB); Ryuzo Yanagimachi, 1425 Ward Ave., Apt. 17W, Honolulu, HI (US) 96822; Takehito Kaneko, 2649 Varsity Pl., #313, Honolulu, HI (US) 96826

( * ) Notice: Subject to any disclaimer, the term of this patent is extended or adjusted under 35 U.S.C. 154(b) by 249 days.

(21) Appl. No.: 10/259,553

(22) Filed: Sep. 27, 2002

(65) Prior Publication Data

US 2003/0215782 A1 Nov. 20, 2003

Related U.S. Application Data

(60) Provisional application No. 60/326,095, filed on Sep. 27, 2001.

(51) Int. Cl.
*A61K 35/52* (2006.01)

(52) U.S. Cl. .......................................... 435/2; 435/1.3

(58) Field of Classification Search ..................... 435/2
See application file for complete search history.

(56) References Cited

U.S. PATENT DOCUMENTS 5,773,217 A * 6/1998 Wangh .......................... 435/6

OTHER PUBLICATIONS

Aisen et al., Theriogenology 53: 1053-1061 (2000).*
Aisen et al., "Effect of Trehalose and EDTA on Cryoprotective Action of Ram Semen Diluents" Theriogenology, 53(5): 1053-61, 2000.
Carroll et al., "Normal Fertilization and Development of Frozen-Thawed Mouse Oocytes: Protective Action of Certain Macromoleculaes" Biol. Reprod., 48:606-12, 1993.
Chatot et al., "Development of 1-Cell Embryos from Different Strains of Mice in CZB Medium" Biol. Reprod., 42:432-40, 1990.
Chatot et al., "An Improved Culture Medium Supports Development of Random-bred 1-Cell Mouse Embryos in vitro" J. Reprod. Fertil., 86:679-88, 1989.
Downs and Mastropolo, "The Participation of Energy Substrates in the Control of Meiotic Maturation in Murine Oocytes" Develop. Biol., 162:154-68, 1994.
Davis et al., "Basic Methods in Molecular Biology", New York: Elsevier, 1986, p. 47 (N/A).
Fairbairn et al., "The Comet Assay: A Comprehensive Review" Mutat. Res., 339:37-59, 1995.
Groigno and Whitaker, "An Anaphase Calcium Signal Controls Chromosome Disjunction in Early Sea Urchin Embryos" Cell, 92:193-204, 1998.
Izant, J.G., "The Role of Calcium Ions During Mitosis" Chromosoma, 88:1-10, 1983.
Kamiguchi and Mikamo, "An Improved, Efficient Method for Analyzing Human Sperm Chromosomes Using Zona-Free Hamster Ova" Am. J. Hum. Genet., 38:724-40, 1986.
Katoh et al., Jpn. J. Genet., 56:357-63, 1981 (N/A).
Kimura and Yanagimachi, "Intracytoplasmic Sperm Injection in the Mouse" Biol. Reprod., 52:709-20, 1995.
Kishikawa et al., "Chromosome Analysis of BALB/c Mouse Spermatozoa with Normal and Abnormal Head Morphology" Biol. Reprod., 61:809-12, 1999.
Kundu et al., "Effect of Dextrans on Cryopreservation of Goat Cauda Epididymal Spermatozoa Using a Chemically Defined Medium" Reproduction, 123 (6):907-13, 2002.
Kuretake et al., "Fertilization and Development of Mouse Oocytes Injectes with Isolated Sperm Heads" Biol. of Reprod., 55:789-95, 1996.
Kusakabe et al., "Detection of Neocarzinostatin-induced Translocations in Human Sperm Chromosomes Using Fluorescence in situ Hybridization of Chromosome 2" Mutat. Res., 369:51-58, 1996.
Maione et al., "Activation of Endogenous Nucleases in Mature Sperm Cells Upon Interaction with Exogenous DNA" DNA Cell Biol., 16:1087-97, 1997.
Martin, et al., "Human Sperm Chromosome Complements after Microinjection of Hamster Eggs" J. Reprod. Fert., 84:179-86, 1988.
Mazur et al., The Enhancement of the Ability of Mouse Sperm to Survive Freezing and Thawing by the Use of High Concentrations of Glycerol and the Presence of an *Escherichia coli* Membrane Preparation (Oxyrase) to Lower the Oxygen Concentration Cryobiology, 40:187-209, 2000.
Nakagata et al., Exp. Anim., 42:317-20, 1993 (N/A).

(Continued)

*Primary Examiner*—Jean C. Witz

(57) ABSTRACT

The present invention provides a composition for freezing or freeze-drying spermatozoa or sperm heads thereof, wherein the composition enables the spermatozoa or sperm heads thereof to maintain chromosome integrity at a temperature of about +4° C. to about −200° C. Also provided is a container containing the composition. The present invention further provides a method for maintaining chromosome integrity of spermatozoa or sperm heads during freezing or freeze-drying. The present invention also provides methods for freezing or freeze-drying spermatozoa to obtain at least one spermatozoan capable of fertilizing an oocyte to produce a live offspring. Also provided are frozen or freeze-dried spermatozoa produced by these methods, and containers containing the frozen or freeze-dried spermatozoa. Finally, the present invention provides methods for producing a live mammalian offspring from an oocyte fertilized with a rehydrated freeze-dried (or thawed or freeze-thawed) spermatozoan.

26 Claims, No Drawings

OTHER PUBLICATIONS

Nakagata, "Cryopreservation of Mouse Spermatozoa" Mammalian Genome, 11:572-76, 2000.
Nakagata et al., "Positive Effect of Partial Zona-Pellucida Dissection on the In Vitro Fertilizing Capacity of Cryopreserved C57BL/6J Transgenic Mouse Spermatozoa of Low Mobility" Biol. Reprod., 57:1050-55, 1997.
Nolan et al., "Implementation of a Large-Scale ENU Mutagenesis Program: Towards Increasing the Mouse Mutant Resource" Mammalian Genome, 11:500-06, 2000.
Ohsako et al., "Comparison of the Nuclear DNA Stability Against Freezing-Thawing and High Temperature Treatments Between Spermatozoa and Somatic Cells" J. Vet. Med. Sci., 59:1085-88, 1997.
Parrington et al., Curr. Topics Dev. Biol., 39:215-43, 1998 (N/A).
Rodriguez et al., "Nuclear Chromatin Decondensation of Spermatozoa in Vitro: A Method for Evaluating the Fertilizing Ability of Ovine Semen" Int. J. Androl., 8(2):147-58, 1985.
Ross et al., "Repeated Freezing and Thawing of Peripheral Blood and DNA in Suspension: Effects on DNA Yield and Integrity" J. Med. Genet., 27:569-70, 1990.
Russo et al., "Further Evidence for the Aneuploidogenic Properties of Chelating Agents: Induction of Micronuclei in Mouse Male Germ Cells by EDTA" Environ. Mol. Mutagen., 19(2):125-31, 1992.
Rybouchkin et al., "Unprotected Freezing of Human Spermatozoa Exerts a Detrimental Effect on Their Oocyte Activating Capacity and Chromosome Integrity" Zygote, 4:263-68, 1996.
Singh et al., "A Simple Technique for Quantitation of Low Levels of DNA Damage in Individuals Cells" Exp. Cell Res., 175:184-91, 1988.
Steele et al., "Comparison of the Effects of Two Methods of Cryopreservation of Testicular Sperm DNA" Fertil. Steril., 74:450-53, 2000.
Sztein et al., "In vitro Fertilization with Cryopreserved Inbred Mouse Sperm" Biol. Reprod., 63:1774-80, 2000.
Sztein et al., "Motility of Cryopreserved Mouse Spermatozoa Affected by Temperature of Collection and Rate of Thawing" Cryobiology, 35:46-52, 1997.
Tada et al., "Cryopreservation of Mouse Spermatozoa in the Presence of Raffinose and Glycerol" J. Reprod. Fertil., 89:511-16, 1990.
Tanaka et al., "Formation of Chromosome-type Alberrations at the First Cleavage After MMS Treatment in Late Spermatids of Mice" Cytogenet. Cell Genet., 31:145-52, 1981.
Tateno et al., "Sonication Per Se Is Not as Deleterious to Sperm Chromosomes as Previously Inferred" Biol. Reprod., 63:341-46, 2000.
Thornton et al., "Large Numbers of Mice Established by in Vitro Fertilization with Cryopreserved Spermatozoa: Implications and Applications for Genetic Resource Banks, Mutagenesis Screens, and Mouse Backcrosses".
Visvardis et al., "Study of DNA Damage Induction and Repair Capacity of Fresh and Cryopreserved Lymphocytes Exposed to H2O2 and gamma-Irradiation With the Alkaline Comet Assay" Mutat. Res., 383:71-80, 1997.
Vishwanath et al., "Do Sperm Cells Age? A Review of the Physiological Changes in Sperm During Storage at Ambient Temperature" Reprod. Fertil. Dev., 9(3):321-31, 1999.
Wakayama et al., "Production of Normal Offspring From Mouse Oocytes Injected With Spermatozoa Cryopreserved With or Without Cryoprotection" J. Reprod. Fert., 112(1):11-17, 1996.
Wakayama and Yanagimachi, "Development of Normal Mice From Oocytes Injected With Freeze-Dried Spermatozoa" Nat. Biotechnol., 16:639-41, 1998.
Wakayama et al., "Production of Normal Offspring From Mouse Oocytes Injected With Spermatozoa Cryopreserved With or Without Cryoprotection" J. Reprod. Fert., 112:11-17, 1998.
Whittingham et al., "Long-term Storage of Mouse Embryos at—196C: the Effect of Background Radiation" Genet. Res. (Camb. ), 29:171-81, 1977.
Wood et al., "High Rates of Survival and Fertilization of Mouse and Hamster Oocytes After Vitrification in Dimethylsulphoxide" Biol. Reprod., 49:489-95, 1993.
Yu et al., "4-Bromo-7-Hydroxyindan Oxime—a New Potent Spermicidal Agent" Int. J. Androl., 10(6):741-46, 1987.

* cited by examiner

FROZEN SPERMATOZOA COMPOSITIONS AND USES THEREOF

RELATED APPLICATION

This application claims the benefit of U.S. Provisional Application No. 60/326,095 filed Sep. 27, 2001, the contents of which are incorporated herein in their entirety.

STATEMENT OF GOVERNMENT INTEREST

This invention was made with government support under NIH Grant No. U0 1HD-38205. As such, the United States government has certain rights in this invention.

BACKGROUND OF THE INVENTION

In studies of mammalian genetics, the mouse is the primary research animal, providing models for the analysis of embryonic development and human genetic diseases. Detailed study of the mouse genome, by techniques involving transgenesis and mutagenesis, is leading to the generation of large numbers of new mouse lines world-wide (Nolan et al., *Mammalian Genome,* 11:500–06, 2000; Thornton et al., *Mammalian Genome,* 10:987–92, 1999). Although more than 1200 mutations, covering a wide range of phenotypes, have been described in the mouse, this represents just a small fraction (1–2%) of the total number of mouse genes.

Since it is not economically or practically possible to maintain unique mouse stocks by conventional breeding, alternative strategies, such as cryopreservation (the technique of freezing tissues, cells, or other biological materials at very low temperatures, such that cells remain membrane-intact and the materials remain genetically stable and metabollically inert), vitrification, and freezing (without cryoprotection) of embryos or oocytes, have been developed to conserve these valuable genotypes for future study. Such methods have inherent difficulties, however, because large numbers of animals are required, and it is often difficult to obtain sufficient numbers of embryos or oocytes. (See, e.g., Carroll et al., *Biol. Reprod.,* 48:606–12, 1993; Wood et al., *Biol. Reprod.,* 49:489–95, 1993).

The use of spermatozoa frozen with cryoprotection as an alternative means to preserve mouse germplasm has gained scientific interest. However, sperm sensitivity to damage during freezing and thawing has proved to be a major limitation to freezing of mouse spermatozoa (Mazur et al., *Cryobiology,* 40:187–209, 2000). Within the last few years, cryopreservation and cryostorage of mouse spermatozoa have been achieved with some degree of success, by use of a cyroprotectant in the medium in which the mouse spermatozoa are suspended or stored (Tada et al., *J. Reprod. Fertil.,* 89:511–16, 1990; Nakagata et al., *Exp. Anim.,* 42:317–20, 1993; Sztein et al., *Cryobiology,* 35:46–52, 1997; Nakagata, *Mammalian Genome,* 11:572–76, 2000; Sztein et al., *Biol. Reprod.,* 63:1774–80, 2000). Unfortunately, though, spermatozoa of some strains remain very difficult to freeze, e.g., C57BIJ6J (Nakagata et al., *Biol. Reprod.,* 57:1050–55, 1997) and BALB/c (Thornton et al., *Mammalian Genome,* 10:987–92, 1999).

Conventional techniques for freezing spermatozoa with cryoprotection often utilize physiological suspension media (e.g., to maintain tissues in a viable state) to suspend spermatozoa prior to freezing. Such media contain specific concentrations of substances that are vital for normal tissue function (e.g., sodium, potassium, calcium, chloride, magnesium, bicarbonate, and phosphate ions, as well as glucose and oxygen), and also have appropriate osmotic pressures. A common example of a physiological medium is Ringer's solution, which is used to maintain organs and tissues alive outside of the animal or human body for limited periods. Ringer's solution is an aqueous solution containing sodium chloride, potassium chloride, and calcium chloride, and has an osmotic pressure the same as that of blood serum. There is, however, no single known physiological medium which can support the survival of tissues and organs of all animal species. For cryopreservation applications, cryoprotectants, including sugars, glycerol, dimethylsulfoxide, propylene glycol, ethylene glycol, methanol, 2,3-butanediol, 1,4-butanediol, and dextrans (ranging from 10 to 2000 kDa), are added to the physiological suspension medium (Kundu et al., *Reproduction,* 123(6):907–13, 2002) in order to maintain cell or tissue viability.

Chelating agents have been used widely in research directed to spermatozoa fertility. In particular, chelating agents have been studied both as fertility inhibitors, e.g., as spermicide additives (Yu et al., *Int. J. Androl.,* 10(6):741–46, 1987), and as fertility promoters, e.g., as enhancers of chromatin decondensation. For example, Rodriguez et al. have demonstrated that the use of chelating agents to bind metal ions that are present in semen results in enhanced chromatin decondensation in ram sperm (Rodriguez et al., *Int. J. Androl.,* 8(2):147–58, 1985). Furthermore, U.S. Pat. No. 5,773,217, issued to L. J. Wangh, discloses use of chromatin-decondensation-enhancing chelating agents to pretreat permeabilized sperm cells prior to sperm-nucleus activation. Nevertheless, chelating agents are also known to exhibit unwanted aneuploidogenic properties that can lead to chromosomal aberrations (Russo et al., *Environ. Mol. Mutagen.,* 19(2):125–31, 1992).

Chelating agents with fertility-promoting properties have also been added to spermatozoa suspension media in non-frozen storage applications. WO 02/24872 describes a nuclear-extraction buffer containing chromatin-decondensation-enhancing chelating agents for washing and storing sperm samples prior to analysis or interaction with other cells or media. However, the addition of chelating agents to an ambient-temperature storage solution, while maintaining the oocyte-penetrating ability of sperm, promotes a high rate of intracellular metabolic activity that may lead to chromatin damage and chromosomal abnormalities (Vishwanath et al., *Reprod. Fertil. Dev.,* 9(3):321–31, 1999). Other studies have utilized chelating agents as an ancillary additive to a physiological medium using trehalose as a cryoprotectant, where the chelating agents prevent cation competition with the cyroprotectant for membrane-binding sites (Aisen et al., *Theriogenology,* 53(5):1053–61, 2000).

To date, no known studies have investigated the protective properties of chelating agents in connection with spermatozoa that have been frozen without cryoprotection, freeze-dried, or freeze-thawed, or demonstrated the ability of chelating agents to preserve the genetic integrity of spermatozoa undergoing the processes of freezing without cryoprotection, freeze-drying, or freeze-thawing.

SUMMARY OF THE INVENTION

In accordance with the present invention, there is provided a composition for freezing or freeze-drying spermatozoa or sperm heads thereof, comprising a buffered medium, an ion-chelating agent, and spermatozoa or sperm heads thereof, wherein the composition enables the spermatozoa or sperm nuclei thereof to maintain chromosome integrity at temperatures ranging from about +4° C. to below −200° C. In one embodiment, the composition is freeze-dried, with a moisture level less than about 5%. Preferably, the buffered solution is a Tris-HCl-buffered to which has been added about 0.1 mM to about 200 mM, preferably about 1 mM to about 100 mM, of a calcium-chelating agent—which is normally used for the preparation of DNA from eukaryotic cells (Davis et al., In *Basic Methods in Molecular Biology* (New York: Elsevier, 1986) p. 47) is added. This composition is effective for storing spermatozoa from strains for which the fertility of spermatozoa frozen conventionally is very poor. A container containing the composition is also provided.

The present invention further provides a method for maintaining chromosome integrity of spermatozoa or sperm heads in a composition during freezing or freeze-drying, by adding an ion-chelating agent to the composition prior to freezing or freeze-drying.

The present invention also provides a method for freezing spermatozoa to obtain at least one spermatozoan capable of fertilizing an oocyte to produce a live offspring, by: (a) collecting live spermatozoa; (b) suspending the spermatozoa in a composition comprising a buffered medium and an ion-chelating agent, to produce a suspension of spermatozoa; and (c) freezing the suspension of spermatozoa, to produce a frozen suspension. The present invention further provides frozen spermatozoa produced by this method, and a container containing the frozen spermatozoa.

Additionally, the present invention provides a method for freeze-drying spermatozoa to obtain at least one spermatozoan capable of fertilizing an oocyte to produce a live offspring, by: (a) collecting live spermatozoa; (b) suspending the spermatozoa in a composition comprising a buffered medium and an ion-chelating agent, to produce a suspension of spermatozoa; (c) freezing the suspension of spermatozoa, to produce a frozen suspension; and (d) drying the frozen suspension of spermatozoa to a moisture level of less than about 5%, to produce freeze-dried spermatozoa. Also provided are freeze-dried spermatozoa produced by this method, and a container containing the freeze-dried spermatozoa.

Finally, the present invention provides a method for producing a live mammalian offspring from an oocyte fertilized with a rehydrated freeze-dried (or thawed or freeze-thawed) spermatozoan, by: (a) isolating a rehydrated freeze-dried (or thawed or freeze-thawed) spermatozoan; (b) inserting the spermatozoan into an isolated oocyte, to form a fertilized oocyte; and (c) allowing the fertilized oocyte to develop into a live offspring.

Additional aspects of the present invention will be apparent in view of the description which follows.

BRIEF DESCRIPTION OF THE FIGURES

[not applicable]

DETAILED DESCRIPTION OF THE INVENTION

The inventors show herein that, following freeze-drying or freezing without cryoprotection, mouse spermatozoa that were suspended in a simple Tris-HCl buffer, containing EGTA (50 mM) and NaCl (50 mM), but no cryoprotectant, maintained their chromosome integrity. In particular, the ability of spermatozoa to activate oocytes spontaneously was not destroyed by freeze-drying or freezing without cryoprotection in this solution. Oocytes were injected with sperm heads from rehydrated freeze-dried and from thawed spermatozoa, and the embryos derived therefrom developed normally. Provided the DNA integrity of the sperm nucleus was maintained during intracytoplasmic sperm injection (ICSI), embryos could be generated from severely damaged spermatozoa that were no longer capable of normal physiological activity. The suspension solution was also effective for preserving spermatozoa from certain strains (C57BL/6J, 129/SvJ, and BALB/c) for which the fertility of spermatozoa frozen conventionally is extremely poor. This technique provides an effective means of storing mouse spermatozoa from many different strains (e.g., inbred, mutant, and transgenic strains), for use in biomedical research.

Accordingly, the present invention provides a composition for freezing spermatozoa or for freeze-drying spermatozoa, comprising a buffered medium, an ion-chelating agent, and spermatozoa or sperm heads thereof, wherein the composition enables the spermatozoa to maintain chromosome integrity at a temperature of about +4° C. to about −200° C. This composition is particularly useful for freezing or freeze-drying spermatozoa when a cryoprotectant (i.e., a substance which is able to maintain cell and/or tissue integrity during freezing) is not utilized, as it has been shown to preserve chromosome integrity at low temperatures where spermatozoa may not otherwise remain membrane-intact. In general, then, the composition of the present invention will be frozen. As used herein, the term “frozen” refers to solidification of a liquid. Thus, the composition of the present invention is frozen when its liquid element has changed to a solid state (e.g., due to a decrease in temperature below the freezing point of the composition). The composition may be rendered frozen by a number of different methods, including freezing without cryoprotection, freeze-drying, and freeze-thawing, as described below. The composition is of particular use where spermatozoa are frozen without cryoprotection (e.g., where conventional freezing, freeze-drying, and freeze-thawing techniques are utilized). In one embodiment of the present invention, the composition is freeze-dried (i.e., frozen and then dried, such that most of the moisture, e.g., 99%, is removed from the frozen composition). For example, the composition may be freeze-dried when its moisture level is less than 0.01%. Preferably, the moisture level of the freeze-dried composition is less than 5%.

The composition of the present invention comprises, among other things, an ion-chelating agent. Preferably, the ion-chelating agent is a divalent-cation chelating agent. Ion-chelating agents are chemical compounds that form complexes with metal ions by serving as multidentate ligands. In particular, an ion-chelating agent is an organic chemical that bonds with free metal ions, and removes them from solutions. A single chelating agent may form several bonds with a single metal ion. Chelator-ion complexes are quite stable in solution, and are common vehicles for transporting metal ions in biological systems. Examples of ion-chelating agents for use in the present invention include, without limitation, EDTA (ethylene diamine tetra-acetic acid), EGTA (ethylene glycol-bis (β-aminoethylether)-N,N,N',N'-tetra-acetic acid), and EGTA-AM (the acetoxymethyl ester of EGTA). The concentration of the ion-chelating agent is preferably between about 0.1 mM and about 200 mM, more preferably between about 1 mM and about 100 mM, and especially between about 40 mM and about 60 mM.

In one embodiment of the present invention, an ion-chelating agent binds ions such as magnesium and calcium. In a preferred embodiment of the present invention, the ion-chelating agent is the calcium-chelating agent, EGTA. Preferred concentrations of EGTA for use in the present invention are described below. In a preferred embodiment of the invention, the ion-chelating agent is EGTA, and the concentration of EGTA is 50 mM.

The composition of the present invention also comprises spermatozoa or sperm heads. These spermatozoa (sperm) and sperm heads may be used to inject and fertilize oocytes, as described below. Accordingly, in order to ensure that as many as possible of the spermatozoa retain their genetic integrity during freezing (e.g., freezing without cryoprotection, freeze-drying, or freeze-thawing), it is preferred that physiologically-mature spermatozoa be used in the composition of the present invention. In mature spermatozoa, DNA is associated with basic proteins called protamines. In mammals, protamines are extensively cross-linked by disulfide bonds. This cross-linking stabilizes the sperm nuclei, and renders them very resistant to physical and chemical disruption. Cross-linking of nuclear protamines occurs mainly during transit of the spermatozoa through the epididymis. Thus, mammalian spermatozoa within the epididymis and in ejaculate (semen) are generally physiologically more mature than those within the testis, and are preferred in the compositions and methods of the present invention—at least in mammals.

Mature spermatozoa from invertebrates and vertebrates are collected by methods known to those skilled in the art. For example, mature spermatozoa of rodents, such as mouse, golden (Syrian) hamster, guinea pig, and the like, may be collected from caudae epididymes; contrastingly, in other species, such as humans, rabbits, pigs, horses, bulls, goats, fowl, and the like, mature spermatozoa may be isolated from freshly-ejaculated semen of fertile males. Spermatozoa of fish (e.g., swordtail, *Xiphophorus helleri*) and invertebrates, such as sea urchins (*Tripneustes gratilla*), may be collected from the testes of mature males.

By way of example, mouse spermatozoa may be obtained from a cauda epididymis by the following method. A cauda epididymis is removed from a mature male mouse (approximately 8 weeks after birth or older). The blood and adipose time are removed from the surface of the cauda epididymis. The cauda epididymis is then compressed to release a dense mass of spermatozoa. A drop (about 2 μl) of sperm mass is placed in the bottom of centrifuge tubes containing 1.5 ml polypropylene, and overlain with 0.5 ml of warm physiological medium (e.g., CZB medium, phosphate-buffered saline (PBS), or isotonic saline). After about 10–20 min at 37° C., motile spermatozoa may be collected from the supernatant.

Additionally, by way of example, spermatozoa may be obtained from semen by the following method. Freshly-ejaculated human semen is allowed to liquefy for about 30 min at room temperature (about 25° C.). The semen is then diluted with about 10 ml of saline, and filtered through about two layers of tissue paper to remove debris. The filtrate may then be centrifuged at 400×g for about 10 min, and the sedimented spermatozoa resuspended in a physiological solution or medium, at a desired concentration, for subsequent freezing (e.g., freezing without cryoprotection, freeze-drying, or freeze-thawing).

Spermatozoa may be obtained from a testis, for example, by the following method. An excised testis is placed in an erythrocyte-lysing buffer (e.g., 155 mM $NH_4Cl$, 10 mM $KHCO_3$, 2 mM EDTA; pH 7.2–7.4), minced using a pair of fine scissors, and filtered through about two layers of tissue paper to remove debris. The filtrate is then centrifuged (e.g., 700×g, for 5 min), and the pellet is resuspended in a physiological medium or solution, at a desired concentration, in preparation for subsequent freezing (e.g., freezing without cryoprotection, freeze-drying, or freeze-thawing).

Regardless of the method used for collection and preparation of the spermatozoa, more than 50% of the recovered spermatozoa should be motile. Once the spermatozoa are recovered, they may be suspended in a physiological medium, as described herein, in preparation for subsequent freezing (e.g., freezing without cryoprotection, freeze-drying, or freeze-thawing). Alternatively, the spermatozoa may undergo further processing to obtain spermatozoan fragments, such as demembranated sperm heads, prior to freezing (e.g., freezing without cryoprotection, freeze-drying, or freeze-thawing).

Demembranated sperm heads are detergent-extracted heads that lack all membranes, including the plasma membrane and inner and outer acrosomal membranes, but retain the nucleus and perinuclear material. For example, sperm heads may be demembranated by treatment with Triton X-100, with or without SDS (sodium dodecyl sulfate). Triton X-100 is a well-known, non-ionic surfactant that is widely used for removal of membrane components under non-denaturing conditions. SDS is an anionic detergent used to solubilize various proteins, including membrane proteins. In the mouse, sperm heads demembranated by Triton X-100 have been shown to be capable of activating oocytes, leading to normal embryonic development.

An exemplary method for suspending spermatozoa in freezing medium follows. Spermatozoa collected from caudae epididymes, testes, or semen, as above, may be allowed to dispense into 1 ml of BM buffer (50 mM NaCl, 50 mM EDTA, and 10 mM Tris-HCl; pH 8.0). In preparation for freezing (particularly freeze-drying), spermatozoa (or demembranated sperm heads) may be suspended in a physiological medium or solution that is sufficient to support the integrity of at least the nucleus of the spermatozoa, under normal conditions.

In view of the foregoing, the suspension medium for spermatozoa must be selected according to the species of interest, in accordance with criteria that are well known to those skilled in the art. Such selection may be made without undue experimentation. When spermatozoa are injected into eggs by micro-manipulation, the spermatozoa do not have to be membrane-intact (they can be "dead") in order successfully to fertilize oocytes by injection, and therefore there is no absolute requirement for a cryopreservative, such as glycerol or the like, in the sperm suspension medium.

Accordingly, the composition of the present invention further comprises, among other things, a buffered medium. As used herein, the term "medium" refers to a solution or other liquid material that is prepared for the growth, maintenance, or storage of biological material. As further used herein, a "buffered medium" is a solution or other liquid material that comprises a chemical capable of maintaining the pH of the solution or medium by absorbing hydrogen ions (which would make it more acidic) or hydroxyl ions (which would make it more basic). For example, in the present invention, use of a buffer may maintain the pH of the composition in a range between 8.0 and 8.6. Preferably, the pH of the composition ranges between 8.2 and 8.4.

The buffered medium of the present invention may be a medium used to suspend or store spermatozoa (e.g., a sperm-suspension medium). While spermatozoa can be suspended in a variety of media, a physiological suspension or storage medium is frequently used. A physiological medium is one that maintains the tissues of an organism in a viable state. Such a medium contains specific concentrations of substances that are vital for normal tissue function (e.g., bicarbonate and phosphate ions, calcium, chloride, glucose, magnesium, oxygen, potassium, and sodium), and also has an appropriate osmotic pressure. One example of a physiological medium is Ringer's solution, which is an aqueous solution containing sodium chloride, potassium chloride, and calcium chloride, and has an osmotic pressure the same as that of blood serum. Other examples of buffered media for use in the present invention include, without limitation, CZB medium, Earle's Balanced Salt Solution (EBSS) (designed for use in a 5% $CO_2$ atmosphere), Hank's Balanced Salt Solution (HBSS) (for use in an air atmosphere in closed containers), Hepes buffer, isotonic saline, phosphate-buffered saline (PBS), Tris-HCl buffer, Tyrode's solution (a salt solution which is a modified Locke solution, comprising NaCl, KCl, $CaCl_2 \cdot 6H_2O$, $MgCl_2 \cdot 6H_2O$, $NaHCO_3$, $NaH_2PO_4$, glucose, and distilled water), and any others described herein. Preferably, the buffered medium is Tris-HCl buffer (e.g., 10 mM Tris-HCl buffer).

The following exemplary solutions, comprising 10 mM Tris-HCl buffer and varying concentrations of NaCl and EGTA, may be used in the composition of the present invention: (1) 20 mM NaCl and 50 mM EGTA; (2) 50 mM NaCl and 50 mM EGTA; (3) 50 mM NaCl and 10 mM EGTA; and (4) 80 mM NaCl and 50 mM EGTA. These solutions may be prepared, for example, from stock solutions of 5 M NaCl, 0.5 M EGTA (pH 8.0, adjusted with NaOH), and 1 M Tris-HCl (pH 7.4) previously made up and diluted with ultrapure water (Millipore Systems). Chemicals may be obtained from Sigma Chemical Co. (St. Louis, Mo.).

The composition of the present invention enables the spermatozoa to maintain their chromosome integrity at temperatures low enough to render the composition frozen (e.g., at a temperature of about −12° C. to about −200° C.). As used herein, the term "maintain chromosome integrity" includes the ability of the spermatozoa or sperm heads to maintain stability in chromosomal structure, and to avoid chromosomal damages, during the freezing, freeze-drying, or freeze-thawing process. In one embodiment, the composition enables the spermatozoa to maintain chromosome integrity at a temperature of about −160° C. to below −200° C., and preferably enables the spermatozoa to maintain chromosome integrity at a temperature of about −196° C. This latter temperature is that of liquid nitrogen, which provides one means for freezing the composition of the present invention. In another embodiment of the present invention, the composition enables the spermatozoa to maintain chromosome integrity at a temperature of about −130° C. to about −150° C., and preferably enables the spermatozoa to maintain chromosome integrity at a temperature of about −132° C. This latter temperature is the glass-transition phase of water, at which all metabolic activity ceases. In yet another embodiment, the composition of the present invention enables the spermatozoa to maintain chromosome integrity at a temperature of about −60° C. to about −80° C., and preferably enables the spermatozoa to maintain chromosome integrity at a temperature of about −70° C. or about −80° C. These latter temperatures are standards for storing frozen biological samples. In a further embodiment of the present invention, the composition enables the spermatozoa to maintain chromosome integrity at a temperature of about −12° C. to about −30° C., and preferably enables the spermatozoa to maintain chromosome integrity at a temperature of about −20° C. This latter temperature is that at which long-term storage of freeze-dried spermatozoa may be appropriate.

The present invention also provides a container containing the above-described composition. The composition may be placed into a variety of differing containers, including, without limitation, an ampoule (e.g., glass), an Eppindorf tube, a glass vial, a microcentrifuge tube, and a plastic cryotube (cryovials). Glass ampoules or plastic cryotubes, for example, may be screw-capped. Alternatively, the sperm suspension may be drawn into plastic straws which, following freeze-drying, may be sealed by a powder sealant, by heat, or with nylon plugs. The volume of sperm suspension in each package is not critical. Typically, a volume of about 50–100 μl is used in a 2 ml ampoule.

As disclosed herein, the inventors have shown that modification of a simple Tris-HCl-buffered solution with high concentrations of a calcium-chelating agent can maintain chromosome integrity in spermatozoa during freeze-drying. This procedure was also effective for storing spermatozoa from strains for which the fertility of spermatozoa frozen conventionally is very poor. Accordingly, the present invention further provides a method for maintaining chromosome stability or genetic integrity of spermatozoa or sperm heads during and throughout the freezing or freeze-drying process, comprising adding an ion-chelating agent to the composition prior to freezing or freeze-drying. As described herein, chromosome integrity is not maintained throughout the freezing or freeze-drying process if lack of stability in the chromosome structure, or a chromosomal aberration, occurs during the process.

The present invention further provides a method for freeze-drying spermatozoa that, upon rehydration, are capable of fertilizing isolated oocytes to produce live offspring. The freeze-dried spermatozoa produced by the method of the invention retain their genetic and reproductive potential, even though, when rehydrated, they are motionless and "dead" in the conventional sense.

During normal fertilization in mammals, a fertilizing spermatozoan ascends the female genital tract, passes through the oocyte's vestments, then fuses with an oocyte. Sperm fusion with the oocyte triggers activation of the oocyte. The activated oocyte resumes meiosis, and oocyte chromosomes transform into a female pronucleus. Meanwhile, the sperm nucleus within the oocyte decondenses to transform into a male pronucleus. Fully-developed female and male pronuclei then unite, and chromosomes from these pronuclei mingle. The resultant zygote develops into a live offspring.

When the whole sperm or isolated sperm heads (i.e., sperm fragments containing all head components, including the nucleus) or the demembranated sperm or sperm heads (i.e., retaining the nucleus and perinuclear materials, but lacking plasma membranes) of the present invention are injected directly into oocytes, normal fertilization and embryonic development also occurs, and this can result in the production of live offspring. Preferably, the sperm head (nucleus) is inserted directly into the cytoplasm of the oocyte. The insertion of the sperm head is by microinjection, preferably by piezo-electrically-actuated microinjection. As discussed further below, embryonic development of the fertilized oocytes of some species may require the simultaneous or sequential injection of a sperm centrosome. If the centrosome does not survive the freeze-drying process, a centrosome may be harvested from an unfrozen spermatozoan, for insertion into the oocyte.

Accordingly, the present invention provides a method for freeze-drying spermatozoa to obtain at least one spermatozoan capable of fertilizing an oocyte to produce a live offspring, comprising the steps of: (a) collecting live spermatozoa; (b) suspending the spermatozoa in a composition comprising a buffered medium and an ion-chelating agent, to produce a suspension of spermatozoa; (c) freezing the suspension of spermatozoa, to produce a frozen suspension; and (d) drying the frozen suspension of spermatozoa to a moisture level of less than about 5%, to produce freeze-dried spermatozoa. This method may further comprise the step of demembranating the spermatozoa, prior to the freezing step, to produce demembranated spermatozoa heads, as described above.

Spermatozoa may be collected and suspended in a buffer composition containing an ion-chelating agent, in accordance with methods described above, in preparation for freeze-drying. For freezing, the suspension of spermatozoa may be frozen slowly or quickly, by known means. For example, the suspension may be frozen in liquid nitrogen vapor, or in the refrigerated air of a mechanical (electrical) freezer, by methods which are well known in the art. Cooling and freezing may be accomplished with a manual static or stepwise regime, or in an electronically-automated and -programmed liquid-nitrogen-fed system. Various rates of freezing (e.g., 1° C.–25° C./minute) may be employed. In one embodiment of the present invention, the freezing step is carried out at −196° C. for 10 minutes.

Various modifications can be used in successful vapor-freezing of the suspension in straws, ampoules, or cryotubes. A metal container (canister) with cigar tubes, or other holders with straws, or holders or racks with ampoules or cryotubes, may be placed directly into liquid-nitrogen vapor, using a liquid-nitrogen refrigerator.

Drying of the frozen sperm suspension, under vacuum, may be accomplished by a variety of different systems known to those skilled in the art. For example, a known apparatus is a VirTis model 10-020 (VirTis Co., Gardiner, N.Y.). The suspension is dried to a moisture level that is less than 5%. The container with freeze-dried spermatozoa is preferably vacuum-sealed, or sealed in the presence of an inert gas, such as nitrogen or argon.

The containers of freeze-dried spermatozoa are preferably stored in the dark, or wrapped with aluminum foil or the like. For long-term storage, it may be preferable to store the containers at temperatures of −20° C. or less. It is expected that, like comparable freeze-dried bacteria, fungi, and the like, the freeze-dried sperm nuclei of the present invention will retain their genetic integrity indefinitely under these storage conditions. However, the containers can be stored at ambient temperature (e.g., room temperature) or ordinary refrigerator temperature (about 4° C.) for periods of time less than, or in excess of, three months, without compromising the ability of the freeze-dried sperm nuclei to fertilize oocytes. Therefore, the freeze-dried sperm can be shipped without the necessity for special conditions or bulky containers. The freeze-dried sperm also may be stored for more lengthy periods of time, including up to one year or even greater than one year.

The method of the present invention may further comprise the step of: (e) rehydrating the frozen suspension of spermatozoa to produce rehydrated spermatozoa, wherein at least one rehydrated spermatozoan is capable of fertilizing an oocyte to produce a live offspring. The freeze-dried-sperm preparation is preferably rehydrated by adding pure water, the volume of which is the same as the original volume of the sperm suspension before freeze-drying. Once rehydrated, any physiological salt solution, such as 0.9% saline or CZB medium (see below), may be used for dilution; the dilution volume is not critical. The concentration of spermatozoa in the final rehydration medium should be sufficient to facilitate the retrieval of individual sperm or individual sperm heads for purposes of sperm injection into oocytes, as described below.

The incidence of oocyte activation and normal fertilization following sperm-head injection appears to decrease with increasing time after sperm rehydration. The allowable time period between rehydration and injection may vary between species; however, by way of example, this time period for mouse spermatozoa is preferably one hour or less.

Freeze-dried, rehydrated spermatozoa are non-motile. Viability of the spermatozoa may be assessed by using any staining method that is capable of distinguishing between spermatozoa that are, in the conventional sense, live or dead. A suitable commercially-available viability test kit for use in the invention is Live/dead FertiLight (Molecular Probes, Eugene, Oreg.), which differentiates between plasma-membrane-intact (live) and plasma-membrane-damaged (dead) cells according to a fluorescence pattern under a UV microscope after staining with propidium iodide/SYBR 14. The nuclei of "live" spermatozoa with intact plasma membranes fluoresce green, whereas those of "dead" spermatozoa fluoresce bright orange-red. It is expected that all of the examined spermatozoa will be "dead" in the conventional sense. The heads and tails of some spermatozoa used in the present method may be separated. The proportion of spermatozoa with broken or missing tails may vary, depending on how gently or roughly the dried specimens are handled during storage. Spermatozoa with or without tails can be used in the injection procedure described below.

The present invention further provides freeze-dried spermatozoa produced by the foregoing method. Also provided is a container containing the freeze-dried spermatozoa produced by this method. As described above, such containers may include, without limitation, an ampoule, an Eppindorf tube, a glass vial, a microcentrifuge tube, and a plastic cryotube.

Additionally, the present invention provides a method for freezing and then thawing (freeze-thawing) spermatozoa to obtain at least one spermatozoan capable of fertilizing an oocyte to produce a live offspring, comprising the steps of: (a) collecting live spermatozoa; (b) suspending the spermatozoa in a composition comprising a buffered medium and an ion-chelating agent, to produce a suspension of spermatozoa; (c) freezing the suspension of spermatozoa, to produce a frozen suspension; and (d) thawing the frozen suspension of spermatozoa to produce thawed spermatozoa, wherein at least one thawed spermatozoan is capable of fertilizing an oocyte to produce a live offspring. The method may further comprise the step of demembranating the spermatozoa, prior to the freezing step, to produce demembranated spermatozoa heads, in accordance with above-described methods. Also provided are freeze-thawed spermatozoa produced by this method, and a container (e.g., an ampoule, an Eppindorf tube, a glass vial, a microcentrifuge tube, and a plastic cryotube) containing the thawed spermatozoa produced by this method.

Freezing and then thawing of spermatozoa results in disruption of their plasma membranes, as assessed by viability-staining techniques that are capable of distinguishing between plasma-membrane-intact (live) and plasma-membrane-damaged (dead) cells. Such freeze-thawed, membrane-disrupted spermatozoa are considered "dead" in the conventional sense. Freeze-thawed spermatozoa may be prepared according to the methods described by Wakayama et al. (*J. Reprod. Fert.*, 112(1):11–17, 1996) and Kuretake et al. (*Biol. of Reprod.*, 55:789–95, 1996). In particular, it has been shown that normal fertile live offspring will develop from mouse epididymal spermatozoa that have been suspended in CZB medium prior to cooling to −20° C. or −50° C. or −196° C., with or without cryoprotectants such as 18% (w/v) raffinose or an ion-chelating agent, stored (frozen) for 1–28 days prior to thawing, and then microinjected into unfertilized oocytes.

In one exemplary method for freeze-thawing mouse epididymal spermatozoa, a composition for freezing or freeze-drying spermatozoa, comprising a buffered medium, an ion-chelating agent, and spermatozoa or sperm heads thereof, is prepared in accordance with methods described above. The composition may be stored (frozen) in a container, for periods ranging from one day to four weeks. For thawing, the container may be removed from the freezer or liquid nitrogen, and placed in water or air at 24–26° C., for about 10 minutes. The thawed sperm suspension is then ready for use in intracytoplasmic sperm injection (ICSI), as described below. Although the method for obtaining freeze-thawed sperm has been described herein for mouse epididymal spermatozoa, one of ordinary skill in the art may adapt the method to spermatozoa from other vertebrates and invertebrates without undue experimentation.

Spermatozoa, or sperm heads thereof, that have been frozen, freeze-dried, or freeze-thawed in accordance with above-described methods may be used to fertilize oocytes using an ICSI or microinjection technique. Accordingly, the present invention further provides a method for producing a live mammalian offspring from an oocyte fertilized with a rehydrated freeze-dried (or thawed or freeze-thawed) spermatozoan, comprising the steps of: (a) isolating a rehydrated freeze-dried (or thawed or freeze-thawed) spermatozoan; (b) inserting the spermatozoan into an isolated oocyte, to form a fertilized oocyte; and (c) allowing the fertilized oocyte to develop into a live offspring. For freeze-dried spermatozoa, the isolating step comprises the substeps of: (i) collecting live spermatozoa; (ii) suspending the spermatozoa in a composition comprising a buffered medium and an ion-chelating agent, to produce a suspension of spermatozoa; (iii) freezing the suspension of spermatozoa, to produce a frozen suspension; (iv) drying the frozen suspension of spermatozoa to a moisture level of less than about 5%; and (v) rehydrating the freeze-dried suspension of spermatozoa. For frozen or freeze-thawed spermatozoa, the isolating step comprises the substeps of: (i) collecting live spermatozoa; (ii) suspending the spermatozoa in a composition comprising a buffered medium and an ion-chelating agent, to produce a suspension of spermatozoa; (iii) freezing the suspension of spermatozoa, to produce a frozen suspension; and (iv) thawing the frozen suspension of spermatozoa.

In one embodiment of the present invention, the step of inserting the spermatozoan further comprises the substep of isolating a sperm head from a sperm tail and inserting the sperm head into the oocyte. In an alternative embodiment, the inserting step further comprises the substep of inserting a spermatozoan centrosome. The step of inserting the spermatozoan into the oocyte may also further include the substep of inserting a non-sperm-derived nucleic acid sequence into the oocyte. The inserting step may be accomplished, for example, by piezo-electrically-actuated microinjection. In an additional embodiment of the present invention, the allowing step comprises the substeps of: (i) allowing the fertilized oocyte to develop into an embryo; and (ii) transplanting the embryo into a foster mother, wherein the foster mother gives birth to the live offspring.

In the methods of the present invention, recipient oocytes for the freeze-dried (or frozen or freeze-thawed) sperm may be obtained, for example, by inducing an animal to ovulate or superovulate by injections of gonadotrophic hormones (for example, sequential administration of equine and human chorionic gonadotrophins) and surgical harvesting of oviductal ova shortly after the expected time of ovulation (e.g., 13–15 hours after injection of human chorionic gonadotrophin in the mouse). Alternatively, ovarian oocytes may be collected and cultured in a medium to allow their maturation, as is known to those skilled in the art. One example of preferred culture medium is modified Eagle's medium (MEM) supplemented with bovine serum albumin (BSA), as described by Downs and Mastropolo (*Develop. Biol.,* 162: 154–68, 1994) for mouse oocytes.

It is known that, in the mouse, normal fertilization can be achieved by injecting isolated sperm heads into oocytes, and that the plasma and acrosomal membranes and all tail components are not essential for normal embryo development. The mouse and, perhaps, most common laboratory rodents are "exceptional" in that a sperm centrosome is not required for normal fertilization and, during normal fertilization, the sperm centrosome in the neck region of the spermatozoan is destined to degenerate within the oocyte after fertilization.

In contrast, in most other eutherian mammals, including cattle and humans, the sperm centrosome plays a central role in the formation of the microtubules—which are essential for the union of male and female pronuclei, and in the subsequent cleavages during embryonic development. Therefore, in these species, the introduction of both a sperm nucleus (head) and a centrosome into an oocyte seems to be essential for the production of normal offspring. It is not presently known whether the sperm centrosome from all species can survive freeze-drying. If not, a centrosome from an unfrozen sperm must be injected into an oocyte, together with the freeze-dried (or frozen or freeze-thawed) sperm head, in order to secure normal embryonic development. Introduction of excessive numbers of centrosomes, however, would result in abnormal pronuclear development and abnormal embryonic development.

The centrosome is normally attached either to the posterior end of the sperm head or to the anterior end of the sperm tail, when the head and tail are separated. Thus, the sperm centrosome may be inserted into the oocyte simultaneously with the sperm head, or inserted by means of simultaneous or consecutive insertion of the sperm tail. Alternatively, insertion of the sperm nucleus and centrosome may be accomplished by insertion of an entire rehydrated spermatozoan into the oocyte.

The entire spermatozoan can be injected into the cytoplasm of a recipient oocyte; however, in species in which the spermatozoa are large, an isolated sperm head (nucleus) is preferably injected directly into the cytoplasm of a recipient oocyte by a microinjection technique. In a preferred method of microinjection of a rehydrated sperm head or a rehydrated demembranated sperm head into a recipient oocyte, the piezo-electrically-driven micropipette is used.

A suitable piezo-electric driving unit is sold, under the name of Piezo Micromanipulator/Piezo Impact Drive Unit, by Burleigh Instruments, Inc. (Burleigh Park, Fishers, N.Y.). The unit utilizes the piezo-electric effect to advance the (injection) pipette holder, in a highly controlled and rapid manner, a very short distance (approximately 0.5 μm). The intensity and duration of each pulse may be varied, and are regulated by a control unit.

For injection into an oocyte, a single spermatozoan is aspirated, tail first, into an injection pipette having a short, flat tip, with an inner diameter of about 5 μm, housed in the piezo-electrically-actuated unit, according to the instructions of the vendor. The sperm head and tail are separated by applying a single or a few piezo pulses to the neck region. The head is then drawn deeply into the pipette.

Throughout the injection of the sperm head (nucleus), the oocyte is anchored by a conventional holding pipette. The tip of the injection pipette containing a selected sperm head is brought into intimate contact with the zona pellucida of an oocyte, and several piezo pulses (using controller-setting scales of intensity 1–5, speed 4–6) are applied to advance the pipette while maintaining a light negative pressure within. When the tip of the pipette has passed through the zona pellucida, the resultant zona plug is expelled into the perivitelline space, and the sperm head is pushed forward until it is near the tip of the pipette. The pipette tip is then apposed to the plasma membrane, and advanced (toward the opposite face of the oocyte), and the holding pipette almost reaches the opposite side of the cortex of the oocyte. The oocyte plasma membrane is now deeply invaginated around the tip of the injection needle. Upon application of one to two piezo pulses (intensity 1–2, speed 1), the oolemma is punctured at the pipette tip, as indicated by a rapid relaxation of the oolemma, which may be clearly visible. The sperm head is then expelled into the ooplasm with a minimum amount (about 6 pL) of accompanying medium. The pipette is then gently withdrawn, leaving the newly-introduced head within the cytoplasm of the oocyte. This method is performed briskly, typically in batches of 10–15 oocytes which, at all other times, are maintained in culture conditions.

Alternative microinjection variants, in which a conventional injection pipette is employed, may be used to inject sperm heads. An example of a suitable microinjection method employing a conventional pipette, for injecting a sperm head into a hamster oocyte, is described by Yanagida et al. (*Biology of Reproduction,* 44:440–47, 1991), the disclosure of which pertaining to such method is hereby incorporated by reference.

Microinjection of the sperm head/demembranated sperm head offers several advantages. First, sperm-head delivery by microinjection is applicable to a wide variety of spermatozoa types, irrespective of size, morphology, and the like. Second, microinjection allows carefully-controlled co-injection (with the donor sperm head) of additional agents into the oocyte at the time of sperm-head injection. These are exemplified below. Third, in the embodiment of the invention wherein insertion of the sperm head is by piezo-electrically-actuated microinjection, rapid and efficient processing of samples is afforded, thereby reducing trauma to sperm and oocytes undergoing manipulation. The oocytes of some species (e.g., mouse) are not amenable to microinjection using conventional needles, whereas piezo-electrically-actuated microinjection affords a high success rate.

It is known that the mouse oocyte can be activated by injection of a single, intact mouse spermatozoan, or its isolated head. Isolated sperm tails are unable to activate the oocyte. In the mouse, active sperm-borne, oocyte-activating factor(s) typically appear during transformation of the round spermatid into the spermatozoan. In some other species, such as humans, this factor may begin to appear before round spermatid stage. The action of these factors is not highly species-specific, because mouse oocytes are activated by injection of spermatozoa from foreign species, such as hamster, rabbit, pig, human, and even fish. It has been reported that one such activating factor is phospholipase C. This protein is readily extractable from mature spermatozoa by simple freezing and thawing. Besides phospholipase C, mature spermatozoa appear to carry another activating factor that is not readily extractable, but may be obtained by sequential treatment of spermatozoa with Triton X-100 and SDS. It is not known whether the readily-extractable phospholipase C and the freeze-thaw extraction-resistant factors are biologically and chemically identical.

It is known that sperm heads sonicated in the presence of Triton X-100 lose all components but the nucleus and perinuclear materials. Yet, when microsurgically injected into oocytes, such Triton-X-100-treated sperm heads (having the nucleus and perinuclear materials, but no plasma membranes) can activate oocytes as efficiently as intact spermatozoa. At least in the mouse, sperm-borne, oocyte-activating molecules appear to be resistant to freeze-drying, because the majority of the oocytes that survive the injection of freeze-dried (or frozen or freeze-thawed) sperm heads are activated and fertilized normally.

If, in other species, injection of the sperm head does not serve to fully activate the oocyte, activation may require additional activators, e.g., electroactivation, or transfer of the oocytes into media containing one or more oocyte-activating substances. Reagents capable of providing an activating stimulus (or combination of activating stimuli) include, but are not limited to, sperm cytoplasmic activating factor, and certain pharmacological compounds (e.g., $Ca^{2+}$ and other signal-transduction modulators), which may be introduced by microinjection after, or concomitant with, injection of the sperm head. Some activating stimuli are provided, following transfer of the fertilized oocytes to media containing one or members of a sub-set of activating compounds, including stimulators of $Ca^{2+}$ release (e.g., caffeine, $Ca^{2+}$ ionophores, such as A 23187 and ionomycin, and ethanol), modulators of phosphoprotein signaling (e.g., 2-aminopurine, staurospurine, and sphingosine), inhibitors of protein synthesis (e.g., A 23187, cycloheximide), 6-dimethylaminopurine, or combinations of the foregoing (e.g., 6-dimethylaminopurine and ionomycin). In one embodiment of the invention, activation of mouse oocytes is achieved by culture of sperm-injected oocytes for 1–6 h in $Ca^{2+}$-free CZB medium containing 2–10 mM $Sr^{2+}$.

Following pronucleus formation, the embryo may be cultured in vitro until it reaches the 2- to 8-cell stage, or morula/blastocyst stage, at which time the embryo may be transferred into the oviduct or uterus of a foster mother.

In one embodiment of the present invention, microinjection of a sperm head into an oocyte permits the introduction—prior to, during, or after the injection of the sperm head into the oocyte—of one or more agents having the potential to alter the developmental outcome of the embryo. For example, ribonucleic acid (RNA) or deoxyribonucleic acid (DNA) may be introduced into the oocyte by microinjection, prior to or following injection of the sperm head. Injection of recombinant DNA harboring the necessary cis-active signals may result in the transcription of sequences present on the recombinant DNA, by resident or co-injected transcription factors, and subsequent expression of encoded proteins, resulting in an antagonistic effect on development inhibitory factors or a positive effect on embryo development. Moreover, the transcript may possess antisense activity against mRNAs encoding development-inhibitory proteins. Alternatively, antisense regulation may be achieved by injecting nucleic acids (or their derivatives) that are able to exert an inhibitory effect by interacting directly with their nucleic acid target(s) without prior transcription within the oocyte.

Recombinant DNA (linear or otherwise) introduced by the method of the present invention may comprise a functional replicon containing one or more expressed, functional genes, under the control of a promoter, exhibiting anything from a narrow to a broad developmental expression profile. For example, a promoter might direct immediate, but brief, expression, where that promoter is active only in the early zygote. Introduced DNA may either be lost at some point during embryonic development, or be integrated at one or more genomic loci and then stably replicated throughout the life of the resulting transgenic individual. In one embodiment of the present invention, DNA constructs encoding putative "anti-aging" proteins, such as telomerase or superoxide dismutase, may be introduced into the oocyte by microinjection. Alternatively, such proteins may be injected directly.

The present invention is described in the following Examples, which are set forth to aid in the understanding of the invention, and should not be construed to limit in any way the scope of the invention as defined in the claims which follow thereafter.

EXAMPLES

The following examples illustrate the compositions of the present invention, and the uses thereof in methods for developing live offspring from oocytes injected with reconstituted freeze-dried spermatozoa. In particular, the examples illustrate the development of normal mice from mouse oocytes injected with the heads (nuclei) of reconstituted freeze-dried mouse spermatozoa. The sperm-suspension medium prior to freeze-drying contained a buffer and an ion-chelating agent, EGTA, as described below.

Example 1

Animals

Gametes were obtained from C57BL/6J, BALB/c, and 129/SvJ inbred and B6D2F1 hybrid mice, aged 8–12 weeks. Random-bred CD-I females, 8–12 weeks old, and mated with vasectomized males of the same strain, were used as recipients for embryo transfer on the first day of pseudopregnancy. All animals were maintained according to the guidelines prepared by the Committee on Care and Use of Laboratory Animals of the Institute Resources National Research Council (DHEW Publication No. [NIH] 80–23, revised in 1985).

Example 2

Reagents and Media

All chemicals were obtained from Sigma Chemical Co. (St. Louis, Mo.), unless otherwise stated.

Solutions comprising 10 mM Tris-HCl buffer and varying concentrations of NaCl and EGTA were used for suspending spermatozoa for freezing and freeze-drying. The concentrations of NaCl and EGTA were as follows: (1) 20 mM NaCl and 50 mM EGTA, (2) 50 mM NaCl and 50 mM EGTA, (3) 50 mM NaCl and 10 mM EGTA, and (4) 80 mM NaCl and 50 mM EGTA. These solutions were referred to as "EGTA media", and were prepared from stock solutions of 5 M NaCl, 0.5 M EGTA (pH 8.0, adjusted with NaOH), and 1 M Tris-HCl (pH 7.4) previously made up and diluted with ultrapure water (Millipore Systems, Burlington, Mass.). The pH of the final EGTA media was 8.2–8.4. The medium for oocyte collection and sperm injection was a modified CZB with 20 mM Hepes buffer, 5 mM $NaHCO_3$, and 0.1 mg/ml polyvinyl alcohol (PVA; cold-water soluble, Mr, 30–50 kDa) instead of bovine serum albumin (BSA) (Hepes-CZB) (Kimura and Yanagimachi, *Biol. Reprod.,* 52:709–20, 1995). After sperm injection, oocytes were cultured in CZB medium (Chatot et al., *J. Reprod. Fertil.,* 86:679–88, 1989; Chatot et al., *Biol. Reprod.,* 42:432–40, 1990) supplemented with 5.56 mM glucose and 5 mg/ml BSA (fraction V) (Calbiochem, San Diego, Calif.). CZB medium was maintained in 5% $C0_2$ in air and Hepes-CZB in air.

Example 3

Sperm Collection, Freezing, and Freeze-Drying

For each experiment, two caudae epididymes of a male were removed and punctured with sharply-pointed forceps. Dense masses of spermatozoa, squeezed from the epididymes, were placed in the bottom of a 1.5-ml polypropylene microcentrifuge tube (flat top) (Fisher Scientific, Pittsburgh, Pa.) containing 1 ml of one of the NaCl/EGTA Tris-HCl-buffered solutions, or 1 ml of CZB or Hepes-CZB culture medium. The tube was incubated for 10 min at 37° C., to allow spermatozoa to disperse. The upper 700–800 μl of the sperm suspension in the tube was collected, and 100 μl aliquots were transferred to either 1.5-ml polypropylene microcentrifuge tubes for freezing, or 2-ml glass ampoules (Wheaton Scientific, Millville, N.J.) for freeze-drying. The microcentrifuge tubes were placed directly in −20° C. or −75° C. freezers, or plunged directly into liquid nitrogen and stored at −20° C. or −75° C. until use. The glass ampoules containing the sperm suspension were plunged into liquid nitrogen for 20 sec, and then connected to a freeze-drying apparatus, the Freeze-dry system (Labconco Co., Kansas City, Mo.). After vacuuming for more than 4 h, each ampoule was flame-sealed. The inside pressure of ampoules at the time of sealing was $32–40\times10^{-3}$ mBAR. The ampoules were stored in the refrigerator at 4° C. until use.

Example 4

Preparation of Oocytes

Female mice were superovulated with intraperitoneal (i.p.) injections of 5 IU eCG and 5 IU hCG (Calbiochem, San Diego, Calif.), given 48 h apart. Oocytes were collected from oviducts between 13 h and 16 h after hCG injection. The oocytes were freed from cumulus cells by treatment with 0.1% bovine testicular hyaluronidase (340 units/mg solid; Sigma Chemical Co. Ltd., St. Louis, Mo.) in Hepes-CZB medium. The oocytes were washed and kept in CZB medium, at 37° C. in 5% $CO_2$ in air, before sperm injection.

Example 5

Preparation of Spermatozoa for ICSI

The frozen sperm samples were thawed by warming the microcentrifuge tubes in a water bath at 37° C. The freeze-dried sperm samples were rehydrated by adding 100 μl ultrapure water to each glass ampoule. A small volume (1–5 μl) of the sperm suspension, taken from the thawed or rehydrated samples, was thoroughly mixed with one drop (5–10 μl) of Hepes-CZB medium containing 12% (w/v) polyvinylpyrorridone (PVP; mw=360,000) (ICN Pharmaceuticals, Inc., Costa Mesa, Calif.). Since EGTA may interfere with normal activation of the oocyte (Izant, J. G., *Chromosoma,* 88:1–10, 1983; Groigno and Whitaker, *Cell,* 92:193–204, 1998), it was important to wash spermatozoa in another drop of the same medium containing 12% PVP, prior to ICSI, to minimize the introduction of EGTA into the oocyte cytoplasm.

Example 6

Intracytoplasmic Sperm Injection

Intracytoplasmic sperm injection (ICSI) was carried out by modifying the technique originally described by Kimura and Yanagimachi (*Biol. Reprod.,* 52:709–20, 1995), viz., the sperm injections were performed at room temperature (25° C.), rather than 17° C. A single spermatozoan was drawn tail first into the injection pipette, and moved back and forth until the head-midpiece junction (the neck) was at the opening of the injection pipette. The head was then separated from the midpiece and tail by applying one or more Piezo pulses (Kimura and Yanagimachi, supra). After the midpiece and tail were discarded, the head was redrawn into the pipette and injected into an oocyte. The heads and tails of many freeze-dried spermatozoa were separated; therefore, their separation by Piezo pulses was unnecessary in most cases. ICSI was completed within 1 h of rehydration of freeze-dried spermatozoa or thawing of frozen spermatozoa.

Example 7

Culture and Examination of Oocytes

Sperm-injected oocytes were transferred into droplets (50–100 μl) of CZB medium under mineral oil (E. R. Squibb and Sons, Inc., Princeton, N.J.), and incubated at 37° C. in a humidified atmosphere of 5% $CO_2$ in air. Oocytes were considered normally fertilized if they contained a second polar body and two pronuclei at 5–6 h after ICSI. The fertilized oocytes were either taken at 6–8 h after ICSI, for incubation with vinblastine for chromosome analysis (see below), or left in culture, for assessing development to the blastocyst stage at 96 h after ICSI. Some of the embryos at the 2-cell stage, i.e., 24 h after ICSI, were transferred to pseudopregnant recipients.

Example 8

Embryo Transfer

Two-cell embryos were transferred into oviducts of pseudo-pregnant CD-1 females (albino) that had mated with vasectomized CD-1 males (albino) the previous night.

Postimplantation development was assessed on day 14 of pregnancy, when the numbers of implantation sites and normally-developing fetuses were recorded. In practice, this provided information on the extent of early embryonic loss after implantation. Normal fetuses at day 14 of pregnancy very rarely fail to develop to full term.

Example 9

Chromosome Analysis

Chromosome preparations were made according to procedures described previously (Kishikawa et al., *Biol. Reprod.,* 61:809–12, 1999; Tateno et al., *Biol. Reprod.,* 63:341–46, 2000). At 6–8 h after ICSI, activated oocytes with two pronuclei and a second polar body were placed in a CZB medium containing 0.006 μg/ml vinblastine, in order to arrest the metaphases of the first cleavage. After treatment with vinblastine for 19–21 h, the zona pellucida was removed with 0.5% pronase (1000 tyrosine units/mg) (Kaken Pharmaceuticals, Tokyo, Japan) before placing the oocytes in a hypotonic citrate solution (1:1 mixture of 30% fetal bovine serum and 1% sodium citrate). Fixation of the oocytes, and spreading of chromosomes onto glass slides, were performed according to the method of Kamiguchi and Mikamo (*Am. J. Hum. Genet.,* 38:724–40, 1986). Structural chromosome aberrations were scored as outlined previously (Kusakabe et al., *Mutat. Res.,* 369:51–58, 1996). The number of aberrations per oocyte was recorded without discriminating between paternal and maternal pronuclei. In this study, only oocytes with 40 chromosomes and without structural chromosome aberrations were recorded as karyotypically normal. Uncountable numbers of aberrations (e.g., chromosome fragmentation and multiple exchanges) were defined as >10 aberrations per oocyte.

Example 10

Analysis of Data

Treatment comparisons were made with the Chi-squared test, using Yates' correction for continuity, and Fisher's exact test where appropriate.

RESULTS

In experiments with B6D2F1 hybrid males, the spermatozoa, at first, swam very actively in the EGTA media; however, motility was gradually lost, and, after 10 min, the spermatozoa were virtually all immotile. Live/dead staining using a Live/Dead viability kit (FertiLight) (Molecular Probes, Inc., Eugene, Oreg.) showed that 70–90% (average 85%) of the spermatozoa were "alive", i.e., plasma membranes were intact, after the 10-min incubation period. The sperm concentration in the dispersed samples was $\sim 1.2 \times 10^6$ spermatozoa/ml.

Table 1 provides a chromosome analysis of fertilized B6D2F1 oocytes that were generated by ICSI using B6D2F1 spermatozoa suspended in different media for freezing and freeze-drying. In the Tris-HCl-buffered medium, concentrations of 50 mM EGTA and 50 mM NaCl were found to be most effective at maintaining chromosome integrity after freezing to −75° C. or −196° C., and after freeze drying. The proportion of normal karyotypes was similar to that obtained with fresh spermatozoa dispersed in either the EGTA medium or Hepes-CZB medium. Chromosomal aberrations increased significantly when spermatozoa were frozen in Hepes-CZB medium alone, or freeze-dried in CZB medium alone. When spermatozoa were frozen in CZB medium alone, there was only a slight reduction in the proportion of normal karyotypes, as compared with fresh spermatozoa in Hepes-CZB medium (92 vs. 81%). Variations in the concentrations of EGTA or NaCl above and/or below 50 mM had an adverse effect on chromosome integrity.

Table 2 presents a chromosome analysis of fertilized B6D2F1 oocytes that were generated by ICSI using 129/SvJ, BALB/c, and C57BL/6J spermatozoa that had been frozen or freeze-dried. The proportion of normal karyotypes obtained with fresh 129/SvJ and BALB/c spermatozoa was significantly higher after dispersion in EGTA medium, as compared with Hepes-CZB medium. There was a significant reduction in chromosome normality with freeze-dried spermatozoa from both of the 129/SvJ and BALB/c strains; this reduction was most pronounced in the 129/SvJ strain. Although fresh C57BL/6J spermatozoa were not examined in this study, a high proportion of normal karyotypes was obtained in oocytes that had been injected with both frozen and freeze-dried spermatozoa.

Table 3 presents the development of embryos generated from B6D2F1 oocytes injected with either fresh, frozen, or freeze-dried B6D2F1 spermatozoa. Activation of the oocytes was reduced after injection with freeze-dried spermatozoa, but the proportion was still extremely high. There was also a slight reduction in the number of 2-cell embryos developing to the blastocyst stage. This may reflect the higher proportion of abnormal karyotypes observed at first cleavage after injecting freeze-dried spermatozoa (~10%).

Table 4 sets forth a summary of the post-implantation development of 2-cell embryos generated by ICSI using fresh, frozen, and freeze-dried spermatozoa from various strains. In all cases, the 2-cell embryos were derived from oocytes and spermatozoa of the same strain. Morphologically-normal, live, 14-day-old fetuses were obtained in all strains using fresh, frozen, and freeze-dried spermatozoa. Overall, the proportion of transferred embryos that implanted was high. Only with embryos derived from fresh 129/SvJ and freeze-dried C57BL/6J spermatozoa was there a significant reduction in implantation. In all strains, early embryonic loss after implantation was similar for embryos from fresh and frozen spermatozoa, and greater for embryos from freeze-dried spermatozoa. The number of fetuses was only reduced with B6D2F1 and C57BL/6J embryos derived from freeze-dried spermatozoa.

As the above-described results show, the inventors have discovered that chromosome integrity of mouse spermatozoa can be maintained during freeze-drying or during freezing without cryoprotection when the spermatozoa are suspended in a simple Tris-HCl-buffered solution containing 50 mM EGTA and 50 mM NaCl. This somewhat "unphysiological" solution is able to afford protection to spermatozoan DNA sufficient to permit normal development of embryos generated from spermatozoa that have been suspended in the solution for storage. The inventors also have evidence (data not shown) indicating that their EGTA medium can maintain the chromosomal integrity of human and rabbit spermatozoa after freeze-drying.

Overall, a high proportion of oocytes (~90%) activated spontaneously after sperm-head injection (data not shown), thereby indicating that the sperm-activating molecules (Parrington et al., *Curr. Topics Dev. Biol.,* 39:215–43, 1998) were not destroyed by freezing or freeze-drying. The proportion of chromosome aberrations was similar to that found after ICSI with fresh spermatozoa (~9%) (Tateno et al., *Biol. Reprod.,* 63:341–46, 2000). Since almost 100% of mouse oocytes fertilized in vivo are karyologically normal (Tanaka et al., *Cytogenet. Cell. Genet.,* 31:145–52, 1981; Katoh et al., *Jpn. J. Genet.,* 56:357–63, 1981), it would appear that the ICSI procedure, per se, independent of freezing or freeze-drying, has some adverse effect upon chromosome stability. With mouse ICSI, the sperm-neck region is damaged (Kimura and Yanagimachi, *Biol. Reprod.* 52:709–20, 1995) or heads are separated from tails (Kuretake et al., *Biol. Reprod.,* 55:789–95, 1996) before injection into the oocytes. It would appear that the resulting damage to the plasma membrane increases the chance of chromosome aberrations occurring in the resulting embryo. Sonication and freezing of human spermatozoa without cryoprotection has been reported to increase chromosome structural aberrations (Martin et al., *J. Reprod. Fert.,* 84:179–86, 1988; Rybouchkin et al., *Zygote,* 4:263–68, 1996). However, it is more likely that prolonged exposure of membrane-damaged spermatozoa to culture media, rather than sonication or cryopreservation themselves, is more detrimental to chromosomal stability (Tateno et al., *Biol. Reprod.,* 63:341–46, 2000).

Freezing and thawing per se do not appear to damage DNA (Whittingham et al., *Genet. Res.* (*Camb.*), 29:171–81, 1977). The DNA integrity of mammalian sperm cells, including those from hamster (Ohsako et al., *J. Vet. Med. Sci.,* 59:1085–88, 1997) and human (Steele et al., *Fertil. Steril.,* 74:450–53, 2000), as well as somatic cells, including those from human blood (Ross et al., *J. Med. Genet.,* 27:569–70, 1990), is maintained during freezing and thawing by methods that achieve optimal rates of cell survival. The comet assay (Singh et al., *Exp. Cell. Res.,* 175:184–91, 1988; Fairbairn et al., *Mutat. Res.,* 339:37–59, 1995) shows that cryopreserved human lymphocytes elicit the same response to the induction of DNA damage by treatment with $H_2O_2$ as do similarly-treated, freshly-isolated human lymphocytes (Visvardis et al., *Mutat. Res.,* 383:71–80, 1997). This suggests that DNA damage is not induced by mechanical or oxidative stress during freezing or freeze-drying; rather, it appears to be induced during the holding period between thawing/rehydration and ICSI.

Enrichment, with $K^+$, of the suspending medium for isolated sperm heads, in order to simulate the intracellular environment, maintained chromosome integrity for periods longer than those maintained in $Na^+$-rich culture media (Kuretake et al., *Biol. Reprod.,* 55:789–95, 1996). It is likely that structural chromosome aberrations are caused by the release of endogenous nucleases from plasma-membrane-damaged spermatozoa following sperm-head isolation, freeze-drying, or freezing without cryoprotection. Maione et al. (*DNA Cell. Biol.,* 16:1087–97, 1997) reported the existence of $Ca^{2+}$-dependent endogenous nucleases in mouse spermatozoa. The presence of the chelating agent, EDTA, and the absence of $Ca^{2+}$ and $Mg^{2+}$ from the $K^+$-rich medium used for isolated sperm heads, probably contributed to the improvement in chromosome stability. Surprisingly, the greatest stability of chromosome structure was obtained with use of an extremely high concentration of EGTA (50 mM). The other Tris-HCl-buffered media with lower or higher levels of $Na^+$ (20 or 80 mM) or a lower concentration of EGTA (10 mM) were much less effective in maintaining sperm-chromosome integrity (Table 1).

The inventors' initial experiences with EGTA media indicated that an EGTA medium with low pH negatively affects chromosome stability. It is not presently known why high pH (8.2–8.4) is important, but it is possible that a high pH assists in repressing the activity of the endogenous endonucleases. Sperm-chromosome aberrations might be further reduced if $Ca^{2+}$ are removed from the injection medium. However, previous reports have not examined the individual effect on sperm-chromosome stability of $Ca^{2+}$, $Mg^{2+}$, $Na^+$, or $K^+$ in the sperm-injection medium.

In connection with the preservation of inbred lines carrying mutations and transgene, it is a great advance to have the ability to preserve spermatozoa from inbred strains that have previously proved difficult to conserve by conventional techniques of freezing and in vitro fertilization. In this study, the inventors have shown that, with relatively few oocytes, a number of viable progeny sufficient to re-establish the strains can be generated after ICSI with freeze-dried and frozen spermatozoa.

The storage of mouse spermatozoa in the freeze-dried state (Wakayama and Yanagimachi, *Nat. Biotechnol.,* 16:639–41, 1998) offers many advantages over cryostorage at −196° C.—a procedure that has been associated with numerous detractions, including difficulty in maintaining a constant supply of liquid nitrogen, and breakdown or contamination of liquid-nitrogen storage containers. In addition, storage at ambient temperatures is inexpensive, and facilitates transport of samples between countries. The inventors have already found that samples can be transported over long distances at ambient temperatures without any increase in chromosome damage or loss of developmental potential (data not shown). Spermatozoa frozen to −75° C., without cryoprotection, generated viable progeny. This also may be a convenient way to store spermatozoa for the short term when liquid nitrogen is unavailable; however, permanent storage at −75° C. is not recommended, since biological activity does not cease until the temperature falls below −130° C.

In conclusion, the preservation of spermatozoa by freeze-drying or freezing in a simple EGTA Tris-HCl-buffered medium provides an important means of maintaining a whole spectrum of mouse strains at low cost, without incurring heritable damage.

While the foregoing invention has been described in some detail for purposes of clarity and understanding, it will be appreciated by one skilled in the art, from a reading of the disclosure, that various changes in form and detail can be made without departing from the true scope of the invention in the appended claims.

TABLE 1

Chromosome analysis of B6D2F1 oocytes fertilized by ICSI with fresh, frozen, or freeze-dried B6D2F1 spermatozoa: comparison of different media for sperm dispersion and storage.

| Medium for sperm dispersion and storage | Sperm treatment | Final freezing temp. (° C.) | Sperm storage Temp. (° C.) | Sperm storage Time (days) | No. oocytes analyzed (exp. no.) | No. chromosome aberrations per oocyte | No. (%) oocyte with normal karyotype |
|---|---|---|---|---|---|---|---|
| Hepes-CZB | Fresh | — | — | — | 145 (9) | 0.083 | 134 (92)[a] |
| | Frozen | −196 | 196 | <1 | 58 (4) | 1.00 | 37 (64)[a] |
| CZB | Frozen | −196 | −196 | <1 | 118 (7) | 0.41 | 96 (81)[b] |
| | Freeze-dried | −196 | 4 | 2 to 63 | 63 (4) | 1.2 | 33 (52)[b] |
| NaCl/EGTA* | | | | | | | |
| 50 50 mM | Fresh | — | — | — | 98 (4) | 0.07 | 91 (93)[c] |
| | Frozen | −20 | −20 | up to 14 | 51 (4) | 0.67 | 37 (73)[c] |
| | | −75 | −75 | up to 14 | 63 (4) | 0.10 | 58 (92) |
| | | −196 | −196 | <1 | 63 (4) | 0.16 | 56 (89) |
| | Freeze-dried | −196 | 4 | up to 21 | 105 (9) | 0.43 | 87 (83)[def] |
| 20 50 mM | Freeze-dried | −196 | 4 | up to 28 | 89 (4) | 0.72 | 60 (67)[d] |
| 80 50 mM | | −196 | 4 | up to 14 | 52 (4) | 1.2 | 28 (54)[e] |
| 50 10 mM | | −196 | 4 | up to 21 | 65 (5) | 3.9 | 12 (18)[f] |

*Varying concentrations of NaCl and EGTA in 10 mM Tris-HCl buffer, pH 8.2–8.4
Statistically significant $X^2$ comparisons: [a,b,e,] and [f]$p < 0.001$; [c]$p < 0.01$; [d]$p < 0.025$

TABLE 2

Chromosome analysis of B6D2F1 oocytes fertilized by ICSI with spermatozoa from 129/SvJ, BALB/c, and C57BL/6J inbred strains after freezing and/or freeze-drying.

| Sperm treatment | Medium for dispersion and storage | Mouse strain | Final freezing temp. (° C.) | Sperm storage Temp. (° C.) | Sperm storage Time (days) | No. oocytes analyzed (exp. no.) | No. chromosome abberrations per oocyte | No. (%) oocytes with normal karyotype |
|---|---|---|---|---|---|---|---|---|
| None (Fresh) | Hepes-CZB | 129/SvJ | — | — | — | 78 (5) | 1.0 | 53 (68)[a] |
| | | BALB/c | — | — | — | 72 (5) | 0.64 | 47 (65)[b] |
| | EGTA* | 129/SvJ | — | — | — | 76 (4) | 0.3 | 64 (84)[ac] |
| | | BALB/c | — | — | — | 61 (5) | 0.066 | 58 (95)[bd] |
| Frozen | EGTA* | C57BL/61 | −75 | −75 | up to 14 | 64 (4) | 0.19 | 55 (86) |
| Freeze-dried | EGTA* | C57BL/6J | −196 | 4 | up to 56 | 92 (5) | 0.55 | 67 (73)[e] |
| | | 129/SvJ | −196 | 4 | up to 42 | 78 (6) | 1.1 | 42 (54)[cef] |
| | | BALB/c | −196 | 4 | up to 42 | 60 (5) | 0.25 | 49 (82)[df] |

*Composition of EGTA medium: 50 mM NaCl, 50 mM EGTA, and 10 mM Tris-HCl
Statistically significant $\chi^2$ comparisons: [b,c,d,] and [f]$p < 0.001$; [e]$p < 0.025$; [a]$p < 0.05$

TABLE 3

In vitro development of B6D2F1 oocytes fertilized by ICSI with fresh, frozen, or freeze-dried B6D2F1 spermatozoa.

| Sperm treatment | Sperm freezing medium | Sperm storage time (days) | No. oocytes Injected (exp. no.) | No. (%) oocytes activated[+] | No. (%) 2-cell embryos | No. (%) blastocysts |
|---|---|---|---|---|---|---|
| Fresh | Hepes-CZB | — | 71 (4) | 71 (100) | 71 (100) | 61 (86)[a] |
| Frozen and kept at −75° C. | EGTA* | up to 112 | 96 (4) | 95 (99) | 94 (99) | 75 (80) |
| Freeze-dried and kept at 4° C. | EGTA | up to 28 | 158 (7) | 135 (85) | 133 (99) | 96 (72)[a] |

*Composition of EGTA medium; 50 mM NaCl, 50 mM EGTA, and 10 mM Tris-HCl
[+]Activated oocytes with 2 pronuclei and the second polar body
Statistically significant $\chi^2$ comparison: [a]$p < 0.05$

TABLE 4

Post-implantation development of oocytes fertilized by ICSI with fresh, frozen, or freeze-dried spermatozoa.

| | | Medium for | Sperm | No. 2-cell | Examination on 14 dpc | | | |
|---|---|---|---|---|---|---|---|---|
| Sperm treatment | Mouse strain | sperm dispersion and storage | storage time (days) | embryos[1] transferred (exp. no.) | No. recipients[2] | No. (%) implants | No. (%) normal fetuses | [range] |
| Fresh | B6D2F1 | Hepes-CZB | — | 94 (8) | 12 | 75 (80) | 54 (57)[b] | [0–83] |
| | C57BL/6J | | — | 48 (6) | 6 | 36 (75) | 26 (54)[c] | [29–73] |
| | 129/SvJ | | — | 54 (4) | 4 | 37 (69) | 22 (41) | [13–58] |
| | BALB/c | | — | 65 (4) | 4 | 36 (55) | 16 (25) | [14–40] |
| Frozen and | B6D2F1 | EGTA[3] | up to 28 | 66 (4) | 8 | 46 (70) | 31 (47) | [14–70] |
| kept at −75° C. | C57BU6J | | up to 28 | 76 (7) | 8 | 68 (89)[a] | 42 (54)[d] | [30–90] |
| | 129/SvJ | | up to 42 | 43 (4) | 4 | 31 (72) | 19 (44) | [38–67] |
| Freeze-dried | B6D2F1 | EGTA[3] | up to 14 | 98 (5) | 8 | 72 (73) | 37 (38)[b] | [11–56] |
| and kept at 4° C. | C57BL/6J | | up to 56 | 176 (17) | 18 | 112 (64)[a] | 43 (24)[cd] | [0–69] |
| | 129/SvJ | | up to 56 | 60 (6) | 6 | 46 (77) | 24 (40) | [27–50] |
| | BALB/c | | up to 35 | 75 (6) | 6 | 58 (77) | 16 (21) | [6–40] |

[1]In all strains, two-cell embryos were derived from syngeneic gametes.
[2]CD-1 females (albino) mated with vasectomized CD-1 males (albino); two-cell embryos transferred on the first day of pseudopregnancy
[3]Composition of EGTA medium: 50 mM NaCl, 50 mM EGTA, and 10 mM Tris-HCl
Statistically significant $\chi^2$ comparisons between treatments within strains: [a,c,] and [d]$p < 0.001$; [b]$p < 0.01$

What is claimed is:

1. A composition for freezing or freeze-drying spermatozoa or sperm heads thereof, comprising a buffered medium, an ion-chelating agent, and spermatozoa or sperm heads thereof, wherein the composition enables the spermatozoa or sperm heads to maintain chromosome integrity at a temperature of about +4° C. to about −200° C., and the pH of the composition is between 8.0 and 8.6.

2. The composition of claim 1, wherein the pH of the composition is between 8.2 and 8.4.

3. A composition for freezing or freeze-drying spermatozoa or sperm heads thereof, comprising a buffered medium, an ion-chelating agent, and spermatozoa or sperm heads thereof, wherein the composition enables the spermatozoa or sperm heads to maintain chromosome integrity at a temperature of about +4° C. to about −200° C. and the composition is freeze-dried.

4. The composition of claim 3, wherein the composition's moisture level is less than about 5%.

5. A method for maintaining chromosome integrity of spermatozoa or sperm beads in a composition during freezing or freeze-drying, comprising adding an ion-chelating agent to the composition prior to freezing or freeze-drying, wherein the pH of the composition is between 8.0 and 8.6.

6. The method of claim 5, wherein the pH of the composition is between 8.2 and 8.4.

7. A method for maintaining chromosome integrity of spermatozoa or sperm heads in a composition during freezing or freeze-drying, comprising adding an ion-chelating agent to the composition prior to freezing or freeze-drying, wherein the composition is freeze-dried.

8. The method of claim 7, wherein the composition's moisture level is less than about 5%.

9. A method for freezing spermatozoa to obtain at least one spermatozoan capable of fertilizing an oocyte to produce a live offspring, comprising the steps of:

(a) collecting live spermatozoa;

(b) suspending the spermatozoa in a composition comprising a buffered medium and an ion-chelating agent to produce a suspension of spermatozoa; and (c) freezing the suspension of spermatozoa, to produce a frozen suspension, and further comprising the step of demembranating the spermatozoa, prior to the freezing step, to produce demembranated spermatozoa heads.

10. A method for freeze-drying spermatozoa to obtain at least one spermatozoan capable of fertilizing an oocyte to produce a live offspring, comprising the steps of:

(a) collecting live spermatozoa;
(b) suspending the spermatozoa in a composition comprising a buffered medium and an ion-chelating agent, to produce a suspension of spermatozoa;
(c) freezing the suspension of spermatozoa, to produce a frozen suspension; and
(d) drying the frozen suspension of spermatozoa to a moisture level of less than 1%, to produce freeze-dried spermatozoa.

11. The method of claim 10, wherein the spermatozoa are collected from a vertebrate.

12. The method of claim 10, further comprising the step of demembranating the spermatozoa, prior to the freezing step, to produce demembranated spermatozoa heads.

13. The method of claim 10, wherein the buffered medium is a physiological suspension medium.

14. The method of claim 10, wherein the buffered medium is Tris-HCl buffer.

15. The method of claim 10, wherein the ion-chelating agent is EGTA.

16. The method of claim 10, wherein the freezing step is carried out at −196° C. for 10 minutes.

17. The method of claim 10, further comprising the step of:

(e) rehydrating the frozen suspension of spermatozoa to produce rebydrated spermatozoa, wherein at least one rehydrated spermatozoan is capable of fertilizing an oocyte to produce a live offspring.

18. The method of claim 17, further comprising the step of storing the freeze-dried spermatozoa for a period of time prior to the rehydrating step.

19. The method of claim 18, wherein the freeze-died spermatozoa are stored at ambient temperature.

20. The method of claim 18, wherein the freeze-dried spermatozoa are stored at about 4° C.

21. The method of claim 18, wherein the freeze-dried sperm are stored at or below −20° C.

22. The method of claim 18, wherein the period of time is up to about three months.

23. The method of claim 18, wherein the period of time is up to one year.

24. The method of claim 18, wherein the period of time is greater than one year.

25. Freeze-dried spermatozoa produced by the method of claim 10.

26. A container containing freeze-dried spermatozoa produced by the method of claim 10.

* * * * *